US012697321B2

(12) United States Patent
Dos Santos Baltazar De Lima et al.

(10) Patent No.: US 12,697,321 B2
(45) Date of Patent: Aug. 4, 2026

(54) Kv1.3 ANTAGONISTS FOR USE IN THE TREATMENT OF CHRONIC AND ACUTE PAIN

(71) Applicant: SEA4US—BIOTECNOLOGIA E RECURSOS MARINHOS, LDA., Sagres (PT)

(72) Inventors: Pedro Afonso Dos Santos Baltazar De Lima, Cascais (PT); Beatriz Szwarc Dos Santos, Lisbon (PT); Ana Rosa Maço Abreu, Pombal (PT); AndréEmanuel Pinheiro Bastos, Lisbon (PT); Marisa Isabel Lopes De Sousa, Benavente (PT); Joana Maria Monteiro Serrão, Charneca da Caparica (PT); Patricia Isabel Da Silveira Maximo, Lisbon (PT); Ana Maria Ferreira Da Costa Lourenco, Lisbon (PT); Miguel Angelo Segão Mondragão, Linda-a-Velha (PT)

(73) Assignee: SEA4US—BIOTECNOLOGIA E RECURSOS MARINHOS, LDA., Null (PT)

( * ) Notice: Subject to any disclaimer, the term of this patent is extended or adjusted under 35 U.S.C. 154(b) by 1194 days.

(21) Appl. No.: 17/631,155

(22) PCT Filed: Jul. 22, 2020

(86) PCT No.: PCT/IB2020/056918

§ 371 (c)(1),
(2) Date: Jan. 28, 2022

(87) PCT Pub. No.: WO2021/019375

PCT Pub. Date: Feb. 4, 2021

(65) Prior Publication Data

US 2022/0280474 A1 Sep. 8, 2022

(30) Foreign Application Priority Data

Jul. 31, 2019 (PT) ........................................ 115686

(51) Int. Cl.
*A61K 31/353* (2006.01)
*A61K 31/37* (2006.01)
(Continued)

(52) U.S. Cl.
CPC ............ *A61K 31/353* (2013.01); *A61K 31/37* (2013.01); *A61K 47/00* (2013.01); *A61P 25/06* (2018.01); *A61P 29/00* (2018.01)

(58) Field of Classification Search
CPC ...... A61K 31/353; A61K 31/37; A61K 47/00; A61K 31/138; A61P 25/06; A61P 29/00
(Continued)

(56) References Cited

U.S. PATENT DOCUMENTS 7,943,649 B2 5/2011 Chau et al.
2007/0021405 A1 1/2007 Abouabdellah et al.
(Continued)

FOREIGN PATENT DOCUMENTS

CN 106146530 11/2016
RU 2376305 C2 12/2009
(Continued)

OTHER PUBLICATIONS

Dyson G., May P. "Chemistry of synthetic drugs", translated from English. Moscow, Mir, 1964, p. 12-19).
(Continued)

*Primary Examiner* — Taylor V Oh
(74) *Attorney, Agent, or Firm* — Arrigo, Lee, Guttman & Mouta-Bellum, LLP; Carla Mouta-Bellum

(57) ABSTRACT

The present patent application relates to the use of antagonists of delayed rectifier potassium ($K^+$) channels, more
(Continued)

specifically Kv1.3 antagonists, as pharmaceutical agents in the treatment, prevention or reduction of both acute and chronic pain. The results and mode of action disclosed herein describe how Kv1.3 antagonists may act as analgesics through reduction of $K^+$ currents rather than their potentiation. With regard to their high efficacy in the treatment of pain, these compounds are highly selective for slow delayed rectifier voltage-activated potassium ($K^+$) currents. Such findings, together with those showing that nitenin, PSORA-4, PAP-1 and AM92016 hydrochloride act as $K^+$ channel blockers and by their effects on $K^+$ current inactivation profiles, also translate into an analgesic effect with reduced side effects. The results disclosed herein show that compounds that inhibit delayed rectifying Kv1.3 channels, such as the ones described herein, are a viable alternative to the already existing pharmaceutical compounds used in the treatment of pain, and specially, in chronic pain.

8 Claims, 11 Drawing Sheets

(51) Int. Cl.
*A61K 47/00* (2006.01)
*A61P 25/06* (2006.01)
*A61P 29/00* (2006.01)

(58) Field of Classification Search
USPC .......................................................... 514/456
See application file for complete search history.

(56) References Cited

U.S. PATENT DOCUMENTS

| | | | | |
|---|---|---|---|---|
| 2011/0275571 | A1* | 11/2011 | Heras Fortuny | A61K 38/168 514/450 |
| 2014/0234343 | A1 | 8/2014 | Lee et al. | |
| 2015/0284405 | A1 | 10/2015 | Trzupek et al. | |

FOREIGN PATENT DOCUMENTS

| | | | |
|---|---|---|---|
| RU | 2421448 | C2 | 6/2011 |
| WO | 02072542 | A2 | 9/2002 |
| WO | 2007009462 | A2 | 1/2007 |
| WO | 2010040803 | A2 | 4/2010 |
| WO | 2015153184 | A1 | 10/2015 |
| WO | 2019083454 | | 5/2019 |
| WO | 2021019373 | A1 | 2/2021 |
| WO | 2021019375 | | 2/2021 |

OTHER PUBLICATIONS

Belikov V.G., Pharmaceutical Chemistry, a course book, 2007, Moscow, Medpress-inform publisher, pp. 27-29.
Mashkovskiy M.D., Drugs, Moscow, Medicine publisher, 1993, Part 1, p. 8.
K.Kümmererer, Pharmaceuticals in the environment, Annual Review of Environment and Resources, 2010, V.35, p. 57-75, doi: 10.1146/annurev-environ-052809-161223 (see abstract, p. 60)).
PCT International Search Report, mailed Nov. 4, 2020, in connection with International Application No. PCT/IB2020/056918, all pages.
PCT Written Opinion, mailed Nov. 4, 2020, in connection with International Application No. PCT/IB2020/056918, all pages.
International Application No. PCT/IB2020/056915, related but not foreign counterpart application: PCT International Search Report, mailed Dec. 12, 2020, 7 pages.
International Application No. PCT/IB2020/056915, related but not foreign counterpart application: PCT Written Opinion, mailed Dec. 12, 2020, 11 pages.
Gouault et al., "Solid-phase Synthesis, Antiviral Activity and Cytotoxicity of Some Functionalized Lactones", Pharmacy and Pharmacology Communications, vol. 5, No. 3, Mar. 1, 1999, 159-163.
Johansson et al., "Biologically Active Secondary Metabolites from the Ascomycete A111-95 2. Structure Elucidation.", The Journal of Antibiotics, vol. 55, No. 1, Jan. 1, 2002, 104-106.
Braun et al., "Synthesis and Determination of the Absolute Configuration of Fugomycin and Desoxyfugomycin: CD Spectroscopy and Fungicidal Activity of Butenolides", Chemistry—A European Journal, vol. 10, No. 18, Sep. 20, 2004, 4584-4593.
Fattorusso et al., "Isolation and structure of nitenin and dihydronitenin, new furanoterpenes from Spongia nitens", Tetrahedron, vol. 27, No. 16, Jan. 1, 1971, 3909-3917.
Heemann et al., "Cytotoxic and Apoptotic Activity of Majoranolide from Mezilaurus crassiramea on HL-60 Leukemia Cells", Evidence-Based Complementary and Alternative Medicine, vol. 2019, Mar. 3, 2019, 1-8.
Alves et al., "Alkene lactones from Persea fulva (Lauraceae): Evaluation of their effects on tumor cell growth in vitro and molecular docking studies", Bioorganic Chemistry, vol. 86, May 31, 2019, 665-673.
Mendgen et al., "Structure-activity relationships of tulipalines, tuliposides, and related compounds as inhibitors of MurA", Oct. 1, 2010, vol. 20, No. 19, 5757-5762.
Song et al., "Homochiral 4-hydroxy-5-hexenoic acids and their derivatives and homologues from carbohydrates", Tetrahedron Asymmetry, Pergamon Press Ltd, Oxford, GB, vol. 12, No. 3, Mar. 5, 2001, 387-391.
Yamamoto et al., "Identification of putative metabolites of docosahexaenoic acid as potent PPAR@c agonists and antidiabetic agents", Feb. 1, 2005, vol. 15, No. 3, 517-522.
EP Examination Report issued Mar. 28, 2024 in foreign related but not counterpart EP Application Serial No. nº 20761628.5 (6 pages).
Fontana, Angelo, et al. "Chemical studies of Cadlina molluscs from the Cantabrian Sea (Atlantic Ocean)" Comp. Biochem. Physiol. vol. 111B, No. 2, pp. 283-290, 1995.
Fontana, Angelo, et al. "Structural and Stereochemical Studies of C-21 Terpenoids from Mediterranean Spongiidae Sponges" J. Nat. Prod. 1996, 59, 869-872.
Lenis, Luis et al. "Isonitenin and Acetylhomoagmatine New Metabolites From the Sponges Spongia Officinalis and Cliona Celata Collected at the Galician Coast (NW Spain)" Natural Product Letters vol. 8. pp. 15-23.
Noyer, Charlotte et al. "Patterns of Chemical Diversity in the Mediterranean Sponge Spongia lamella" PLoS One, Jun. 2011 | vol. 6 | Issue 6 | e20844, pp. 1-11.
Rueda, Ana et al. "New Metabolites from the Sponge Spongia agaricina" J. Nat. Prod. 1998, 61, 258-261.
English translation of CN106146530A.
Langlais et al. Scope and Limitations of Xanthate—Mediated Synthesis of Functional γ-Thialactones, ACS Omega, 3 (12), 17732-17742 (2018).
NPL_CAS1629451_87_1.
Spela, Gubic et al., "Immunsuppresive effects of thiophene-based KV1.3 inhibtors" European Journal of Medicinal Chemistry, vol. 259 Nov. 1, 2023 p. 115561 (17 pages).
Hanson et al. J Pharmacol Apr. 1999UK-78,282, a novel piperidine compound that potently blocks the Kv1.3 voltage-gated potassium channel and inhibits human T cell activation;126(8):1707-16.
Nguyen et al. Mol Pharmacol. Dec. 1996Novel nonpeptide agents potently block the C-type inactivated conformation of Kv1.3 and suppress T cell activation; 50(6):1672-9 (https://molpharm.aspetjournals.org/content/50/6/1672).
Tarcha et al. J Pharmacol Exp Ther Sep. 2012 Durable pharmacological responses from the peptide ShK-186, a specific Kv1.3 channel inhibitor that suppresses T cell mediators of autoimmune disease; 342(3):642-53.
Bartok et al. Toxicon Sep. 2014Margatoxin is a non-selective inhibitor of human Kv1.3 K+ channels:87: 6-16.

* cited by examiner

+ 40 mV
- 70 mV
-120 mV control

PAP-1

τ~302ms subtraction 1 nA 200 ms

+ 40 mV
- 70 mV
-120 mV

AM92016 hydrochloride subtraction 1 nA 200 ms

Kv1.3 ANTAGONISTS FOR USE IN THE TREATMENT OF CHRONIC AND ACUTE PAIN

CROSS-REFERENCE TO RELATED APPLICATIONS

This application is a U.S. National Stage Entry of PCT/IB2020/056918, filed Jul. 22, 2020 and claims priority to Portuguese Patent Application No. 115686, filed Jul. 31, 2019, both of which are herein incorporated by reference in their entirety.

TECHNICAL FIELD

The present disclosure relates to the use of antagonists of delayed rectifier potassium ($K^+$) channels, more specifically Kv1.3 blockers as pharmaceutical agents in the treatment, prevention or reduction of both acute and chronic pain.

BACKGROUND ART

Acute pain usually arises suddenly and the cause is specific. It is sharp in quality. Acute pain commonly does not last longer than tree—six months. It goes away when there is no longer an underlying cause for the pain. A person can then go on with life as usual. Exemplary causes of acute pain include surgery, broken bones, dental work, burns and cuts, labor and childbirth.

Chronic pain is defined as pain persisting for more than three months or beyond the natural recovery time. Pain signals keep firing into the nervous system, even without physiological stimuli, for weeks, months or years. It arises in many medical conditions, including for example diabetes, arthritis, migraine, fibromyalgia, cancer, back pain, shingles, sciatica, trigeminal neuralgia and previous trauma or injury. Chronic pain can cause disability significantly interfering with a person's quality of life and causing a huge negative impact on society. It affects 21% of the world's population (1.5 billion people) and has enormous economic costs associated. In the United States of America (USA) alone, in 2010, it was estimated that there were $560-635 billion spent in salary losses and low productivity, and health care costs. With increasing aged population, the demand for adequate and better pain management therapies is on the rise.

Although there are effective and safe analgesics for mild pain, treatments for moderate and severe chronic pain are, in most cases, ineffective and cause limiting and noxious side effects. Therefore, the major problem for patients of most types of chronic pain is the inexistence of a truly adequate pharmaceutical treatment, at least without inflicting important limiting side-effects. For example, against situations of moderate to severe pain levels, opioid derivatives do alleviate pain but co-inflict important noxious effects like habituation, addiction and loss of drive or motivation. The use of opioids became an epidemical problem in several countries, with increasing addiction situations and a heavy burden for the society. For example, in USA, the number of deaths related to opioids use is much greater than the number of deaths caused by illicit drugs. Other kinds of drugs are used for treatments, including antidepressants, antiepileptic drugs, and non-steroidal anti-inflammatory drugs (NSAIDs), but these are either not efficient enough or also cause relevant side-effects.

Other, such as more recent treatments for moderate to severe pain, closer to the pharmacological context of the present invention, include ion channel modulators. Ion channels are key proteins present in neuronal membranes that shape electrical signaling, and thus, pain signals in nerves. Neurons involved in pain sensing (nociception) located in the peripheral nervous system include those that have their cell bodies located in the nervous ganglia (dorsal root ganglia-DRG, outside the spinal cord or trigeminal ganglia-TG, in the head). Such nociceptive fibers are the first peripheral nerve sensors involved in the physiological pathway that leads to the brain perception of pain.

In terms of currently available therapies involving ion channels modulation for the treatment of pain, there are only two cases already in the market.

Notwithstanding, they are only partially effective or still cause side effects, due to the type of ion channel being modulated. Such medications are:

Topic capsaicin, a Transient Receptor Potential Cation channel subfamily V member 1 (TRPV1) channel agonist;

Intrathecal injection of ziconotide (Prialt®), a N-type voltage-gated calcium channel blocker, obtained from a marine cone snail; in this case, acting not peripherally, but centrally.

New products currently under clinical development (in the pipeline of several biotechnology and pharmaceutical companies but which have not been approved for commercialization) include new opioids with certain modifications (making them less addictive) and other ion channel modulators tackling ion channels known to be involved in pain, but more adequate than TRPV1 and N-type voltage-gated calcium channels (e.g. ion channels such as other TRPs, voltage-gated sodium channels $Na_v1.7$ and $Na_v1.8$).

To date, there are only two agents acting on a $K^+$ channel that are currently under non-clinical or clinical trials for pain treatment.

a) The anticonvulsant retigabine (Phase II) attenuates nociceptive behaviors in rat models of persistent and neuropathic pain. Retigabine works primarily as a $K^+$ channel opener—that is, by activating a certain family of voltage-gated potassium (Kv7/M) channels in the brain.

b) Other channel modulator BL-7050 (pre-clinical phase), based on the molecular structure of diclofenac (a NSAID) binds to and stabilizes the body's potassium channels, controlling their hyper-excitability (by keeping it open) and preventing the occurrence of pain by keeping the channels open for the outflow of $K^+$.

However, despite substantial pharmaceutical research, there is still a need for clinically approved ion channels that are better and specific blockers/potentiators, leaving patients with no alternative besides pharmaceutical drugs with heavy side-effects.

SUMMARY

In one aspect, the present disclosure relates to the use of compounds that are antagonist of delayed rectifier channels, in particular the Kv1.3 channel, as analgesics for the treatment, prevention or reduction of chronic pain and acute pain.

Without wanting to be bound by theory, in some aspects, the present invention differentiates from the presently existing solutions not only by its chemical nature but also by its mode of action.

By "switching off" or by reducing the activity of the nociceptive fibers with bioactive molecules, brain perception of pain may be blocked or attenuated, but in a manner that may not affect brain functioning, because these molecules would act in the peripheral portion of the pain signaling pathway, prior to the central nervous system. Examples of such molecules are described herein.

Thus, in one embodiment, the disclosure relates to the discovery that antagonists for the delayed rectifier $K^+$ channel Kv1.3 have analgesic properties and are particularly efficient for chronic pain.

Any aspect or embodiment described herein may be combined with any other aspect or embodiment as disclosed herein. While the present invention has been described in conjunction with the detailed description thereof, the foregoing description is intended to illustrate and not limit the scope of the present invention, which is defined by the scope of the appended claims. Other aspects, advantages, and modifications are within the scope of the following embodiments/claims.

Embodiment 1. Compounds that are antagonists of the slow delayed rectifier Kv1.3 channel, pharmaceutical salts or prodrugs thereof, for use as analgesics in the treatment, prevention or reduction of chronic pain and acute pain.

Embodiment 2. Compounds that are antagonists of the slow delayed rectifier Kv1.3 channel, pharmaceutical salts or prodrugs thereof, for use as analgesic in the treatment, prevention or reduction of chronic pain and acute pain, wherein said compounds have an affinity 2.5 times greater for a Kv1.3 channel than for any other Kv1.x channel, specifically Kv1.1, Kv1.2, Kv1.4, Kv.1.5, Kv1.6 and Kv1.7.

Embodiment 3. Compounds that are antagonists of the slow delayed rectifier Kv1.3 channel, pharmaceutical salts or prodrugs thereof, for use in the treatment, prevention or reduction of pain, wherein the compounds are at least one of nitenin, PSORA-4, PAP-1, AM92016 hydrochloride, their analogues, salts, or combinations thereof.

Embodiment 4. Compounds that are antagonists of the slow delayed rectifier Kv1.3 channel, pharmaceutical salts or prodrugs thereof, are used in warm-blooded vertebrates, preferably mammals, more preferably humans.

Embodiment 5. Compounds that are antagonists of the slow delayed rectifier Kv1.3 channel, pharmaceutical salts or prodrugs thereof, for use in the treatment, prevention or reduction of pain in an individual in need thereof, more specifically with acute or chronic pain. Acute and chronic pain is intended to include, but is not limited to, at least one of the following: neuropathic pain, nociceptive pain, psychogenic or somatogenic pain, diabetic neuropathic pain, post-herpetic pain, low-back pain, radiculopathy pain, musculoskeletal pain, post-operative and post-traumatic pain, phantom pain, surgical pain, wound associated pain, chemotherapy-induced peripheral neuropathic pain, short-term/acute or long-term/chronic inflammatory pain, rheumatic pain, arthritic pain, pain associated with osteoarthritis, myofascial pain, migraine, orofacial chronic pain, trigeminal neuralgia, pain associated with cancer, pain associated with fibromyalgia, hyperalgesia syndromes, pain associated with infections, HIV related pain, sprains and strains, hyperalgesia, somatogenic pain, psychogenic pain, heat induced pain, physical pain, nociceptive pain, rheumatic pain, headache, pelvic pain, myofascial, vascular pain, migraine wound, wound associated pain, arthritic pain, somatic visceral pain, phantom pain, radiculopathy, lumbar pain, visceral pain, bowel pain, bladder pain and pain associated with osteoarthritis.

Embodiment 6. A pharmaceutical composition comprising a pharmacologically acceptable diluent or carrier and a combination of active ingredients (e.g, excipients), wherein said active ingredients comprise a therapeutically effective dosage of at least one of nitenin, PSORA-4, PAP-1, AM92016 hydrochloride or a pharmacologically acceptable salt or prodrug thereof.

Embodiment 7. A method of treating chronic pain or acute pain in a subject in need thereof, comprising administering to the subject a therapeutically effective amount of a compound that is an antagonist of the slow delayed rectifier Kv1.3 channel.

Embodiment 8. The method of embodiment 7, wherein said compound has an affinity 2.5 times greater for a Kv1.3 channel than for any other Kv1.x channel, by at least one affinity-measuring method.

Embodiment 9. The method of any one of embodiments 7 and 8, wherein the compound is chosen from nitenin, PSORA-4, PAP-1, AM92016 hydrochloride, their analogues, salts, or combinations thereof.

Embodiment 10. The method of any one of embodiments 7 through 9, wherein the subject is a warm-blooded vertebrate, preferably a mammal, more preferably a human.

Embodiment 11. The method of any one of embodiment 7 through 10, wherein the acute and chronic pain are chosen from neuropathic pain, nociceptive pain, psychogenic or somatogenic pain, diabetic neuropathic pain, post-herpetic pain, low-back pain, radiculopathy pain, musculoskeletal pain, post-operative and post-traumatic pain, phantom pain, surgical pain, wound associated pain, chemotherapy-induced peripheral neuropathic pain, short-term/acute or long-term/chronic inflammatory pain, rheumatic pain, arthritic pain, pain associated with osteoarthritis, myofascial pain, migraine, orofacial chronic pain, trigeminal neuralgia, pain associated with cancer, pain associated with fibromyalgia, hyperalgesia syndromes, pain associated with infections, HIV related pain, sprains and strains, hyperalgesia, somatogenic pain, psychogenic pain, heat induced pain, physical pain, nociceptive pain, rheumatic pain, headache, pelvic pain, myofascial, vascular pain, migraine wound, wound associated pain, arthritic pain, somatic visceral pain, phantom pain, radiculopathy, lumbar pain, visceral pain, bowel pain, bladder pain and pain associated with osteoarthritis.

The Figures presented below aim to illustrate the (1) the blockage effect of four compounds on the voltage-activated $K^+$ currents recorded from the small diameter Dorsal Root Ganglia neurons (sdDRGns) (FIGS. 1-4), (2) the hyperpolarizing effects of three compounds on curves of the voltage sensitivity of the steady-state inactivation of the $K^+$ currents recorded from sdDRGns (FIG. 4-6), and, (3) the in vivo data, the effects of three compounds on the sensitivity to mechanical stimuli as a score of pain.

FIG. 1, FIG. 2 and FIG. 3 illustrate the effect of nitenin (0.29 μM), PSORA-4 (3 nM), PAP-1 (2 nM) and AM92016 hidrochloride (40 nM), respectively, on voltage activated currents recorded from sdDRGns. In sdDRGns, voltage-activated outward potassium ($K^+$) currents were evoked by a depolarizing step to +20 mV (holding potential of −70 mV) preceded by a hyperpolarizing pre-pulse to −120 mV. Currents were better fit by the sum of two exponential functions, thus revealing two components (here termed $I_{slow}$ and $I_{fast}$)

whose time constants (i) were of tens of milliseconds for $\tau_{fast}$ and hundreds of milliseconds for $\tau_{slow}$.

BRIEF DESCRIPTION OF DRAWINGS

For easier understanding of this application, figures are attached in the annex that represent exemplary forms of implementation, which nevertheless are not intended to limit the technique disclosed herein.

The relationships were better fit with the sum of two Boltzmann functions, showing that in both conditions there are two components: one more hyperpolarized component (component 1) and one other more depolarized component (component 2). In fact, the Vh parameters (voltage of half maximum current) of the Boltzmann equation showed more hyperpolarized values when during PAP-1 treatment (control: Vh1=−90.1 mV Vh2=−27.8 mV; PAP-1: Vh1=−101.7 mV Vh2=−32.6 mV).

Figure 1:
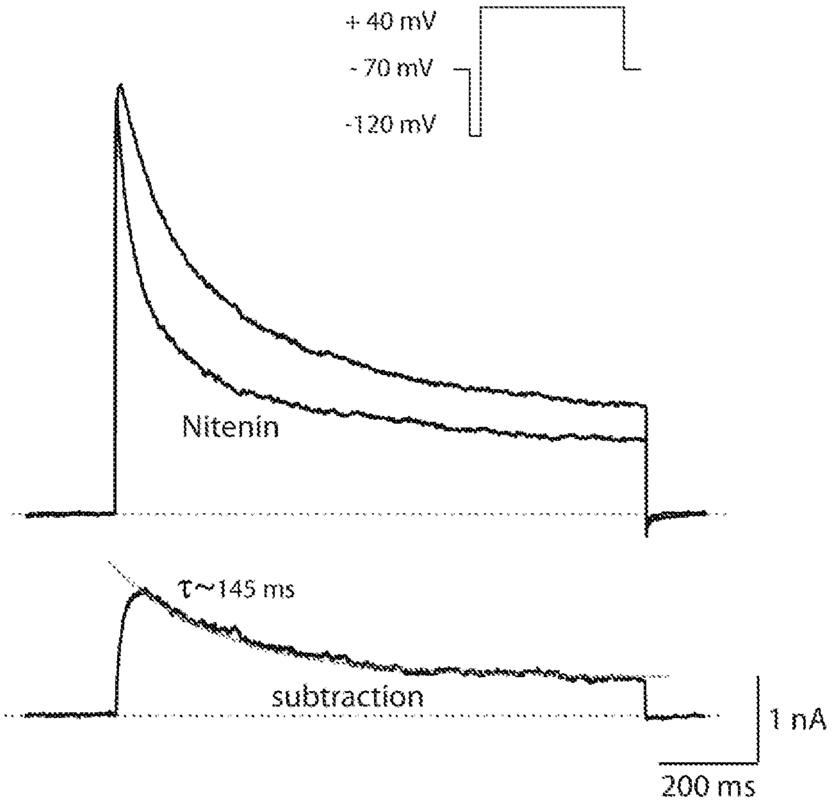
FIG. 1 shows a typical voltage activated $K^+$ current traces recorded before and in the presence of nitenin (0.1 μg/ml; 0.29 μM); lower trace corresponding to the current subtraction, fit with a single-exponential function (time constant τ~150 ms).
Figure 2:
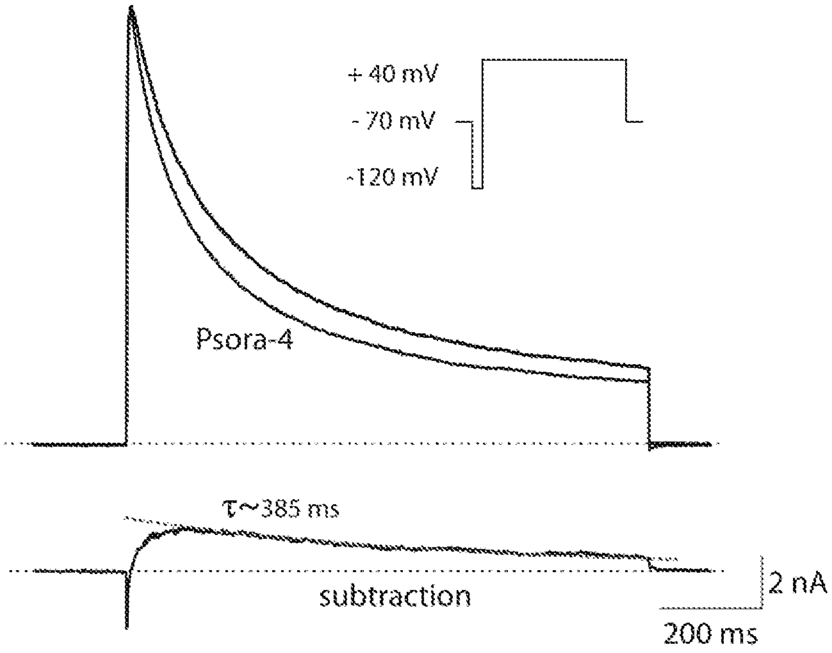
FIG. 2 shows a typical voltage activated $K^+$ current traces recorded before and in the presence of PSORA-4 (1 ng/mL; 3 nM); lower trace corresponding to the current subtraction, fit with a single-exponential function (time constant τ~385 ms).
Figure 3:
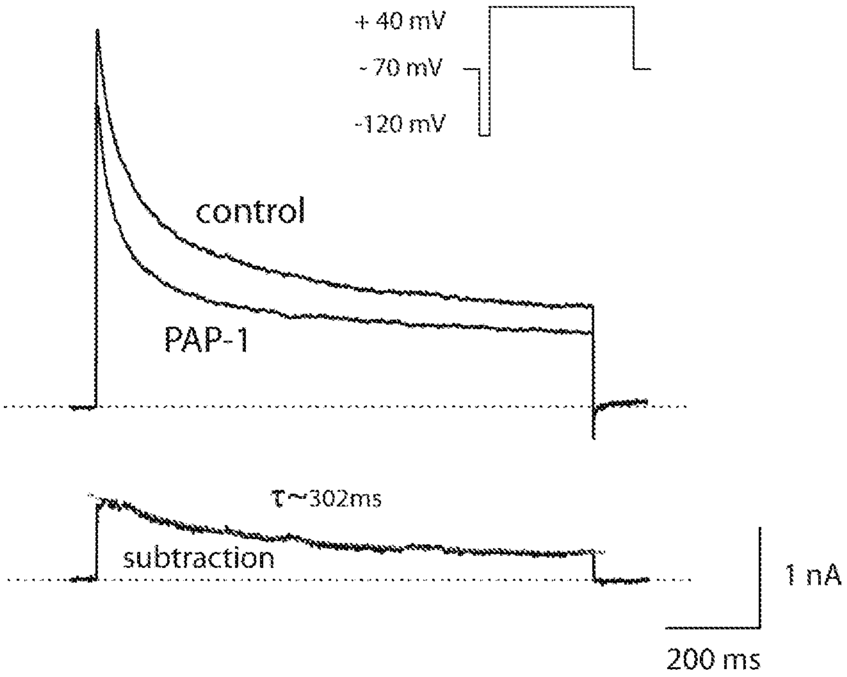
FIG. 3 shows a typical voltage activated $K^+$ current traces recorded before and in the presence of PAP-1 (0.7 ng/mL; 2 nM); lower trace corresponding to the current subtraction, fit with a single-exponential function (time constant τ~302 ms).
Figure 4:
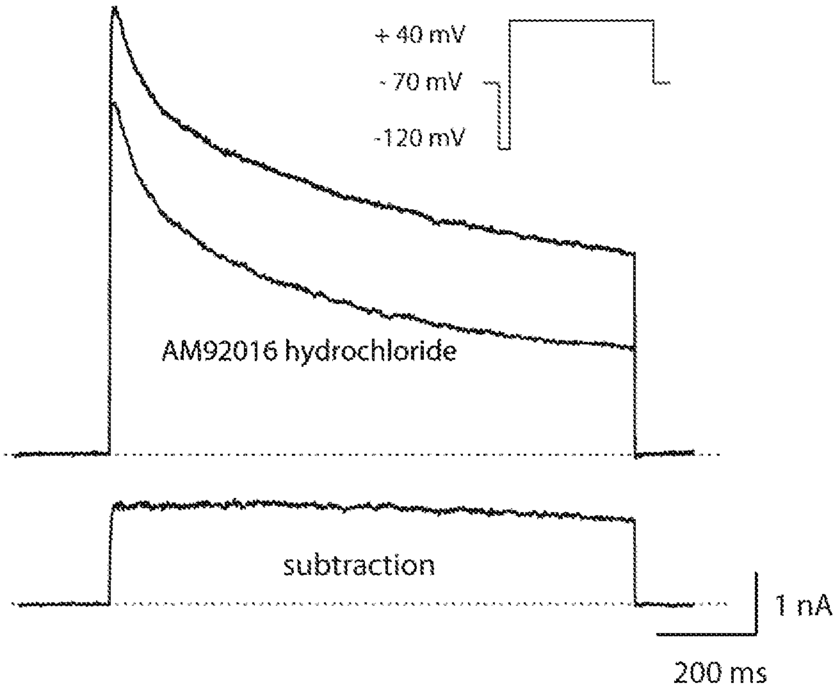
FIG. 4 shows a typical voltage activated $K^+$ current traces recorded before and in the presence of AM92016 hidrochloride (19.4 ng/mL; 40 nM); lower trace corresponding to the current subtraction).
Figure 5:
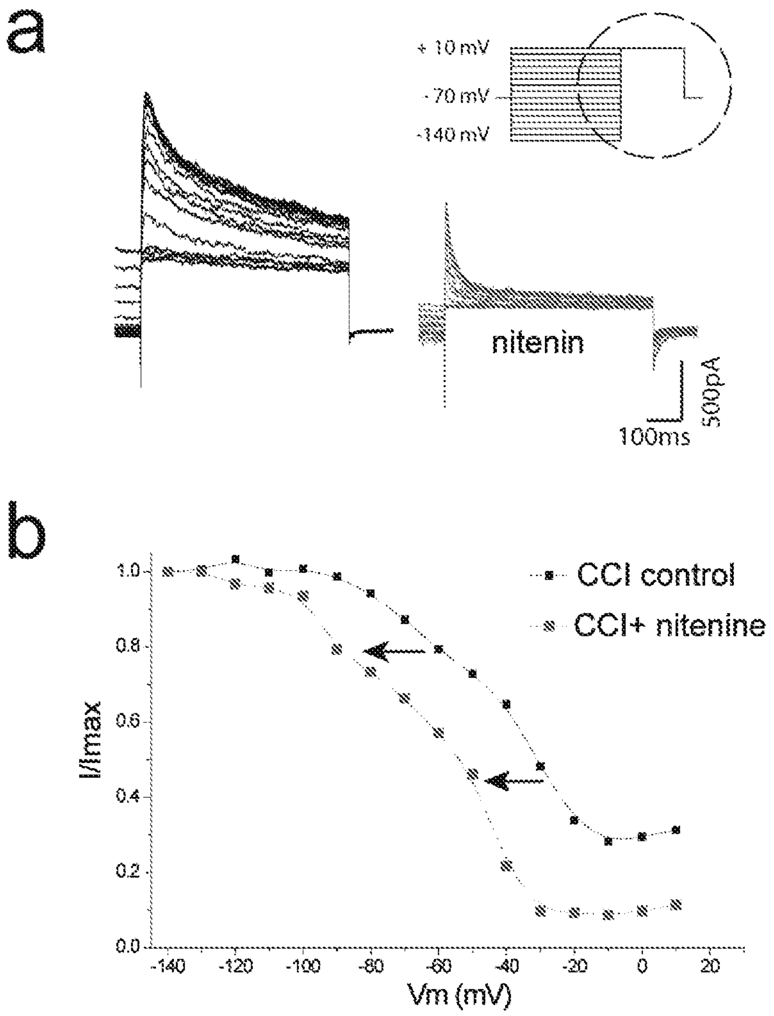
FIG. 5 shows a typical effect of nitenin on the voltage dependence of steady state of inactivation of the $K^+$ currents recorded from a small diameter neuron isolated from a dorsal-root ganglion isolated of the 'affected' side of a CCI rat model 28 days after surgery. a) Current traces were elicited during a command pulse to +10 mV (600 ms) preceded by a series pre-pulses of 1040 s duration, ranging from −140 to +10 mV in a 10 my step increments; traces in the left (black) were obtained before and those on the right (in grey), during the application of nitenin ((0.1 μg/ml; 0.29 μM)). b) Current/voltage relationships where current peak amplitudes (obtained in 'a') are plotted against the potentials of the pre-pulse used in the voltage protocol in 'a' (bullets in black relate to control-CCI; bullets in grey, during nitenin treatment). One can observe a shift to hyperpolarized values during the nitenin treatment. The relationships were better fit with the sum of two Boltzmann functions, showing that in both conditions there are two components: one more hyperpolarized component (component 1) and one other more depolarized component (component 2). In fact, the Vh parameters (voltage of half maximum current) of the Boltzmann equation showed more hyperpolarized values when during nitenin treatment (control: Vh1=−73.3 mV Vh2=−26.3 mV; nitenin: Vh1=−95.3 mV Vh2=−47.0 mV).
Figure 6:
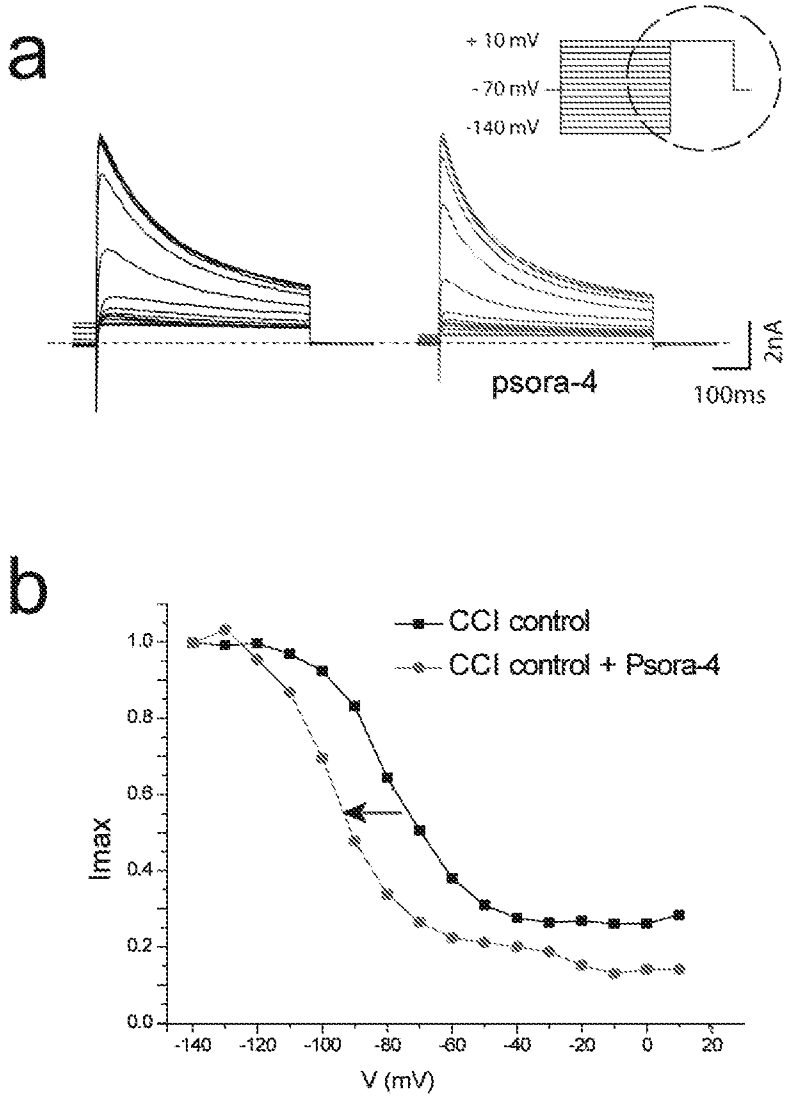
FIG. 6 shows a typical effect of Psora-4 (1 ng/mL; 3 nM) on the voltage dependence of steady state of inactivation of the $K^+$ currents recorded from a small diameter neuron isolated from a dorsal-root ganglion isolated of the 'affected' side of a CCI rat model 28 days after surgery. a) Current traces were elicited during a command pulse to +10 mV (600 ms) preceded by a series pre-pulses of 1040 s duration, ranging from −140 to +10 mV in a 10 my step increments; traces in the left (black) were obtained before and those on the right (in grey), during the application of Psora-4 (1 ng/mL; 3 nM). b) Current/voltage relationships where current peak amplitudes (obtained in 'a') are plotted against the potentials of the pre-pulse used in the voltage protocol in 'a' (bullets in black relate to control; bullets in grey, during Psora-4 treatment). One can observe a shift of the relationship to hyperpolarized values during the Psora-4 treatment. The relationships were, in this case, better fit with a single Boltzmann. In fact, the Vh parameters (voltage of half maximum current) of the Boltzmann equation showed more hyperpolarized value when during Psora-4 treatment (control: Vh=−78.3 mV; Psora-4: Vh=−95.5 mV).
Figure 7:
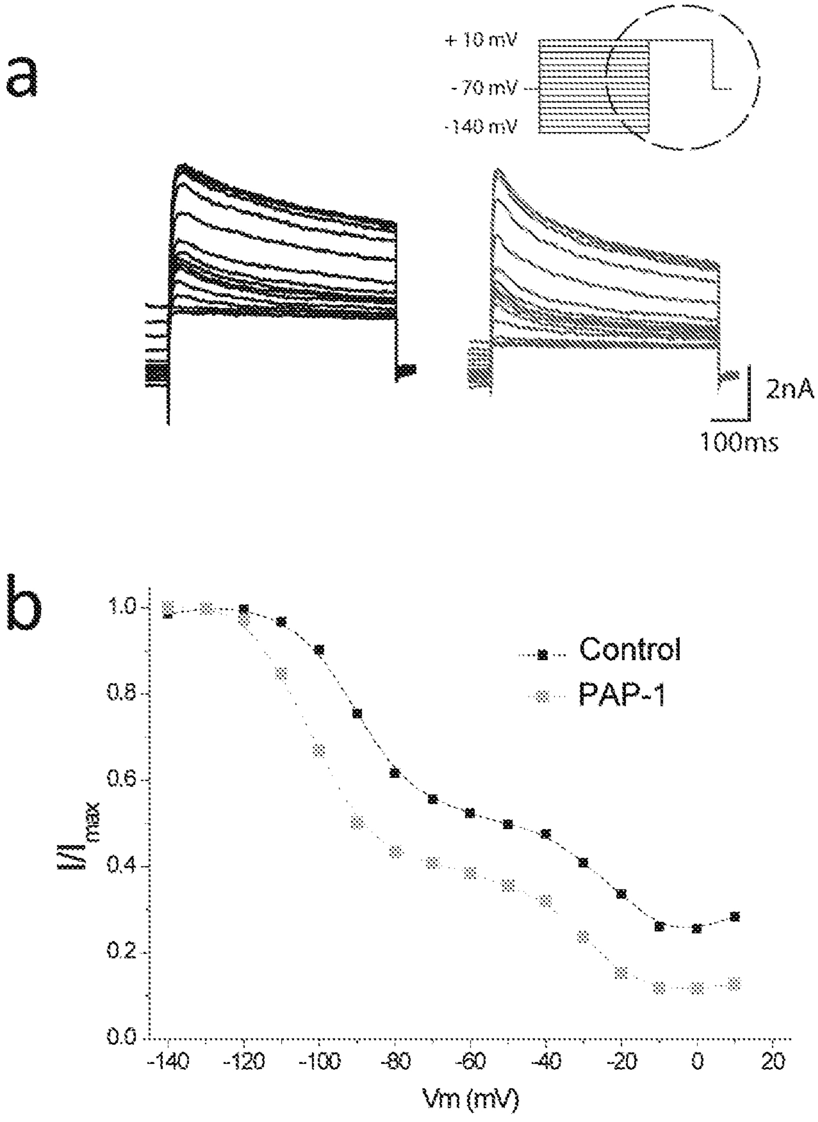
FIG. 7 shows a typical effect of PAP-1 (0.7 ng/mL; 2 nM;) on the voltage dependence of steady state of inactivation of the $K^+$ currents recorded from a small diameter neuron isolated from a dorsal-root ganglion isolated of the 'affected' side of a CCI rat model 28 days after surgery. a) Current traces were elicited during a command pulse to +10 mV (600 ms) preceded by a series pre-pulses of 1040 s duration, ranging from −140 to +10 mV in a 10 my step increments; traces in the left (black) were obtained before and those on the right (in grey), during the application of PAP-1 (0.7 ng/mL; 2 nM). b) Current/voltage relationships where current peak amplitudes (obtained in 'a') are plotted against the potentials of the pre-pulse used in the voltage protocol in 'a' (bullets in black relate to control; bullets in grey, during PAP-1 treatment). One can observe a shift of the relationship to hyperpolarized values during the PAP-1 treatment.
Figure 8:
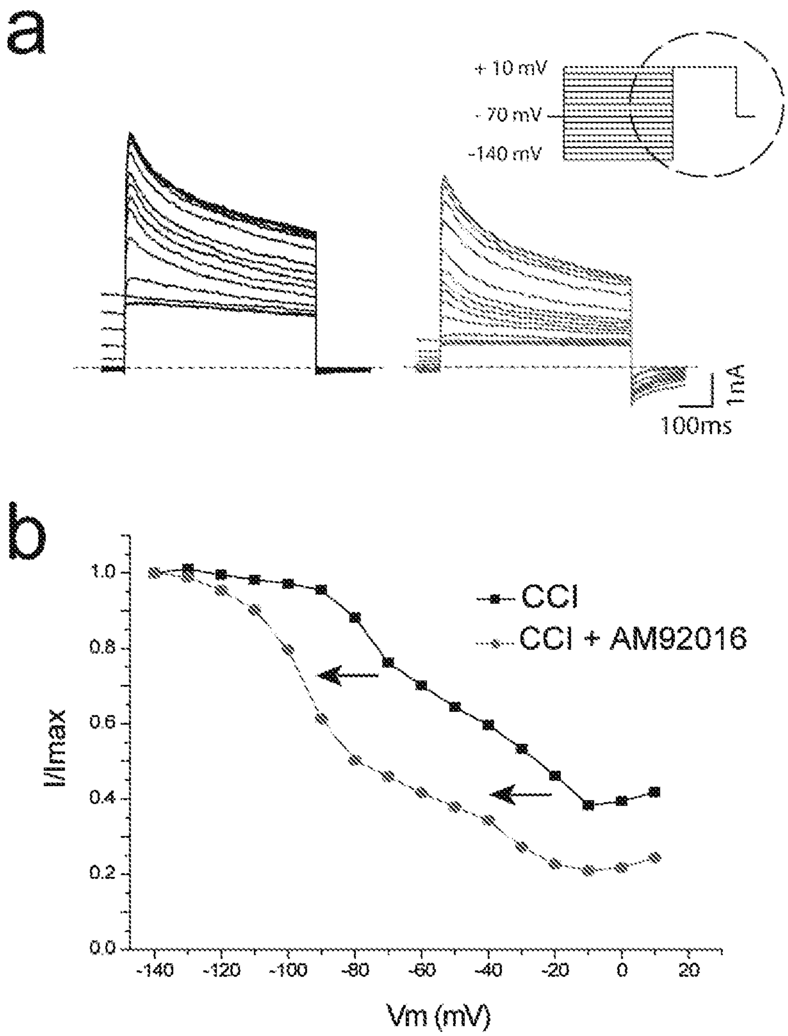

FIG. 8 shows a typical effect of AM92016 hidrochloride (19.4 ng/mL; 40 nM) on the voltage dependence of steady state of inactivation of the $K^+$ currents recorded from a small diameter neuron isolated from a dorsal-root ganglion isolated of the 'affected' side of a CCI rat model 28 days after surgery. a) Current traces were elicited during a command pulse to +10 mV (600 ms) preceded by a series pre-pulses of 1040 s duration, ranging from −140 to +10 mV in a my step increments; traces in the left (black) were obtained before and those on the right (in grey), during the application of AM92016 hidrochloride (19.4 ng/mL; 40 nM). b) Current/voltage relationships where current peak amplitudes (obtained in 'a') are plotted against the potentials of the pre-pulse used in the voltage protocol in 'a' (bullets in black relate to control-CCI; bullets in grey, during AM92016 hidrochloride treatment). One can observe a shift to hyperpolarized values during the AM92016 hidrochloride treatment. The relationships were better fit with the sum of two Boltzmann functions, showing that in both conditions there are two components: one more hyperpolarized component (component 1) and one other more depolarized component (component 2). In fact, the Vh parameters (voltage of half maximum current) of the Boltzmann equation showed more hyperpolarized values when during the treatment of AM92016 hidrochloride (control: Vh1=−71.3 mV, Vh2=−28.2 mV; AM92016 hidrochloride: Vh1=−93.63 mV Vh2=−33.6 mV).

Figure 9:
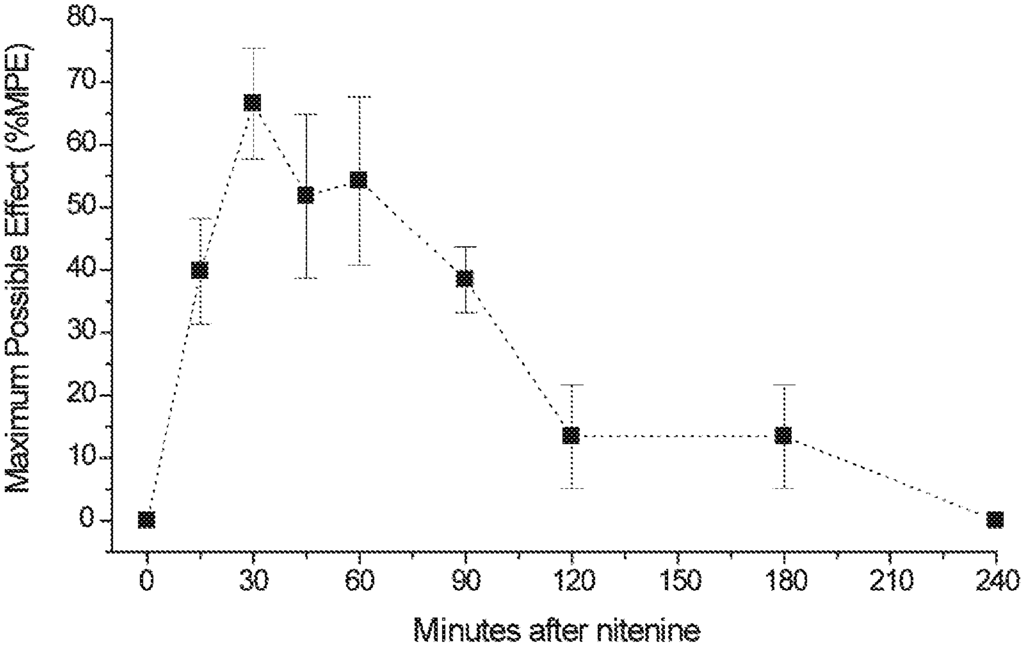

FIG. 9 illustrates behavioral readouts as measures of pain during treatment with nitenin on a neuropathic pain rat model CCI (chronic constriction injury). Typical experiment using a group of Wistar rats subjected to four unilateral sciatic nerve constrictions. Values refer to the mechanical sensitivity to stimulation using calibrated Von Frey Filaments; black filled markers relate to scores obtained from the ipsilateral, operated leg but ponder the values found in the contralateral, uninjured leg as well the scores obtained before the induction of the model (% Maximum Possible effect, Altun A, 2015). The Graphic shows the effect of intravenous injection of nitenin (estimated plasma concentration of 1 μg/ml) on the mechanical sensitivity of the ipsilateral leg. The effect is maximum at around 30 sec to 1 h after injection, reaching values, in some instances similar to those obtained during baseline, prior to surgery. The experiment presented, follows the induction of the model showing that the mechanical sensitivity of the ipsilateral limb increases markedly, whereas the one associated with the contralateral leg remained unchanged, similar to baseline values. This tendency is maintained during 26 days after surgery, day that treatment with nitenin was performed (data not presented).

Figure 10:
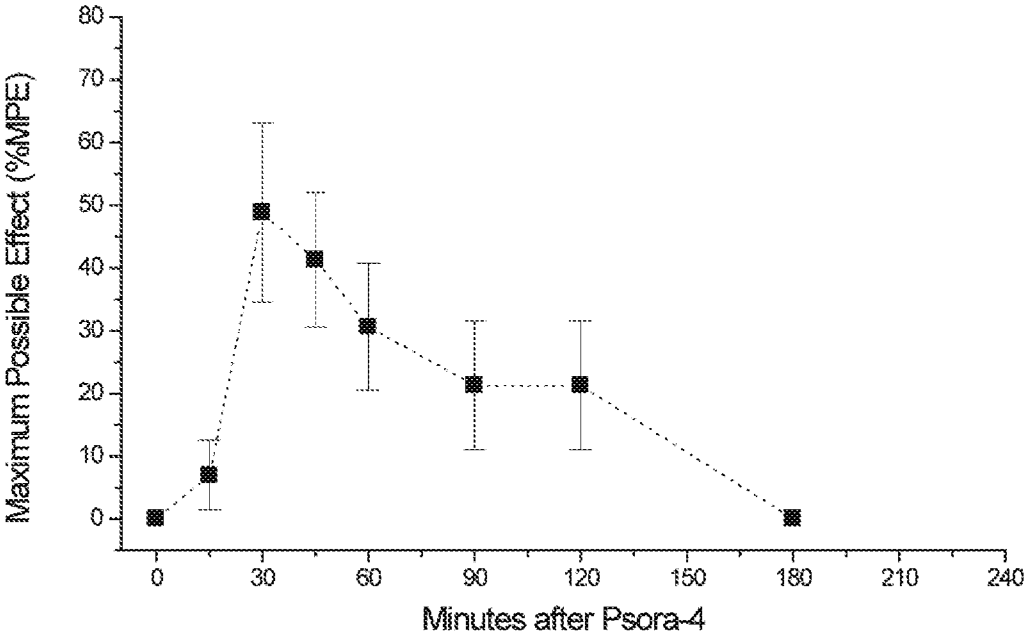

FIG. 10 illustrates behavioral readouts as measures of pain during treatment with Psora-4 on a Neuropatic pain rat model CCI (Chronic constriction injury). Typical experiment using a group of Wistar rats subjected to four unilateral sciatic nerve constrictions. Values refer to the mechanical sensitivity to stimulation using calibrated Von Frey Filaments; black filled markers relate to scores obtained from the ipsilateral, operated leg but ponder the values found in the contralateral, uninjured leg as well the scores obtained before the induction of the model (% Maximum Possible effect, Altun A, 2015). The Graphic shows the effect of intravenous injection of Psora-4 (estimated plasma concentration of 30 μg/ml) on the mechanical sensitivity of the ipsilateral leg. The experiment presented, follows the induction of the model showing that the mechanical sensitivity of the ipsilateral limb increases markedly, whereas the one associated with the contralateral leg remained relatively unchanged. This tendency is maintained during 34 days after surgery, day that treatment with Psora-4 was performed (data not presented).

Figure 11:
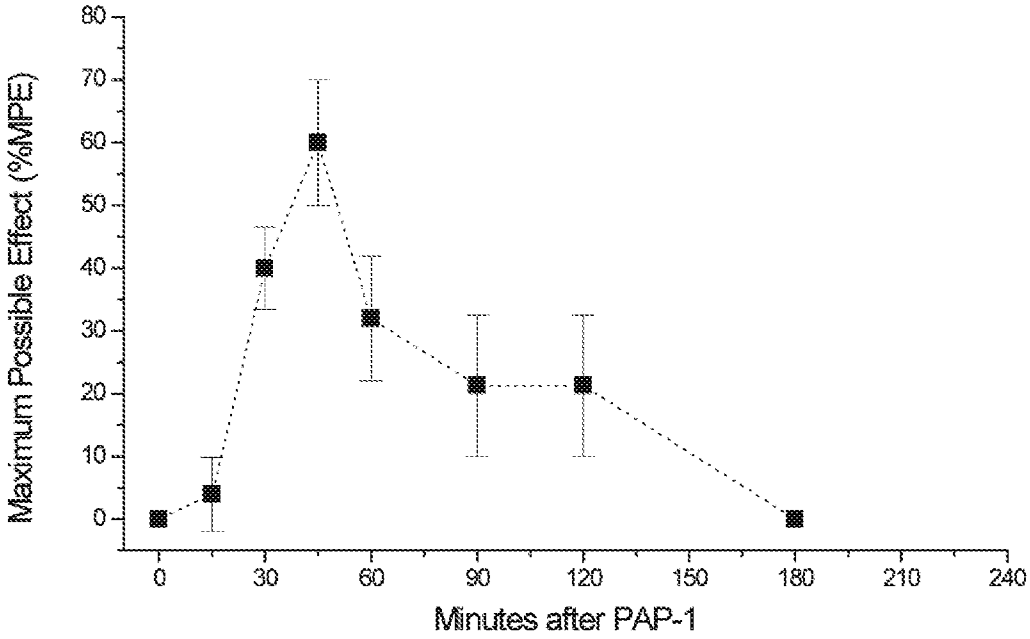

FIG. 11 illustrates behavioral readouts as measures of pain during treatment with PAP-1 on a Neuropatic pain rat model CCI (Chronic constriction injury). Typical experiment using a group of Wistar rats subjected to four unilateral sciatic nerve constrictions. Values refer to the mechanical sensitivity to stimulation using calibrated Von Frey filaments; black filled markers relate to scores obtained from the ipsilateral, operated leg but ponder the values found in the contralateral, uninjured leg as well the scores obtained before the induction of the model (% Maximum Possible effect, Altun A, 2015). The Graphic shows the effect of intravenous injection of Psora-4 (estimated plasma concentration of 30 μg/ml) on the mechanical sensitivity of the ipsilateral leg. The experiment presented, follows the induction of the model showing that the mechanical sensitivity of the ipsilateral limb increases markedly, whereas the one associated with the contralateral leg remained relatively unchanged. This tendency is maintained during 22 days after surgery, day that treatment with PAP-1 was performed (data not presented).

Figure 12:
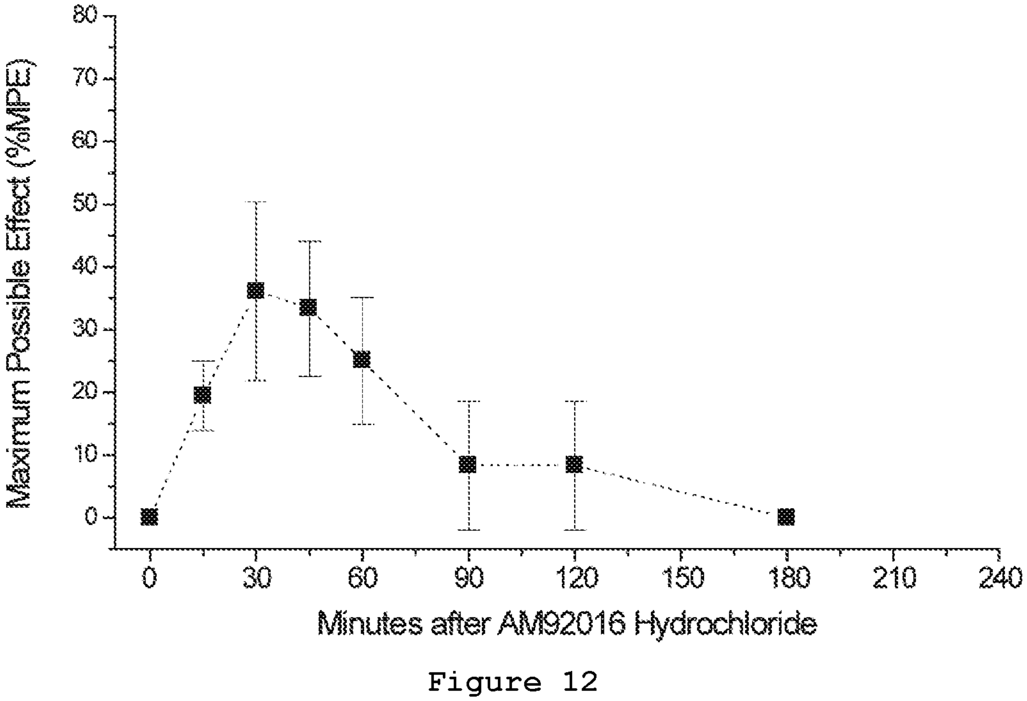

FIG. 12 illustrates behavioral readouts as measures of pain during treatment with AM92016 hidrochloride on a Neuropatic pain rat model CCI (Chronic constriction injury). Typical experiment using a group of Wistar rats subjected to four unilateral sciatic nerve constrictions. Values refer to the mechanical sensitivity to stimulation using calibrated Von Frey Filaments; black filled markers relate to scores obtained from the ipsilateral, operated leg but ponder the values found in the contralateral, uninjured leg as well the scores obtained before the induction of the model (% Maximum Possible effect, Altun A, 2015). The Graphic shows the effect of intravenous injection of AM92016 hidrochloride (estimated plasma concentration of 2.9 μg/ml) on the mechanical sensitivity of the ipsilateral leg. The experiment presented, follows the induction of the model showing that the mechanical sensitivity of the ipsilateral limb increases markedly, whereas the one associated with the contralateral leg remained relatively unchanged. This tendency is maintained during 28 days after surgery, day that treatment with AM92016 hidrochloride was performed (data not presented).

DETAILED DESCRIPTION

As used in this application, except as otherwise expressly provided herein, each of the following terms shall have the meaning set forth below. Additional definitions are set forth throughout the application.

This disclosure relates to the use of antagonists of the slow delayed rectifier Kv1.3 channel as analgesics for the treatment, prevention or reduction of chronic and acute pain. Thus, in the context of the present disclosure, the compounds referred to as "Kv1.3 antagonists", "Kv1.3 blocking compounds" or "Kv1.3 blockers" are used herein interchangeably and should be understood as any compound that inhibits/antagonises slow delayed rectifying $K^+$ channels, preferably the delayed rectifier Kv1.3 channel; specifically, it relates to compounds with an affinity at least 2.5 times greater to Kv.1.3 than to any other Kv1.x channel, specifically Kv1.1, Kv1.2, Kv1.4, Kv.1.5, Kv1.6 and Kv1.7. In some embodiments, the compound has an affinity that is 3 times, 5 times, 10 times, 20 times, or 100 times greater for human Kv.1.3 channel than for any other Kv1.x, specifically Kv1.1, Kv1.2, Kv1.4, Kv.1.5, Kv1.6 and Kv1.7.

In the context of this disclosure, "affinity" relates to the effect on the activity of such channel. Affinity can be measured by voltage clamp recordings of currents evoked by cells that express solely that given channel.

Voltage-clamp recordings under the whole-cell configurations were/are used to measure the 'amount of inhibition' of the whole-cell current evoked by a given channel expressed in non-excitable cell lines. Dose responses are obtained by measuring such inhibitions per each concentration. Voltage-activated K+ currents were evoked from mammalian cell lines expressing Kv1.1, Kv1.2, Kv1.3, Kv1.4, Kv1.5, kv1.6 or kv1.7 using standard voltage protocols (Schmitz et al., 2005; Vennekamp et al.).

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone). It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of an agent to a subject, using any of the various methods and delivery systems known to those skilled in the art. Exemplary routes of administration for the compounds disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the compound is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

A "therapeutically effective amount," "effective dose," or "effective amount," of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By "therapeutically effective dosage" it is meant that the administration of that dosage, either in a single dose or multiple dose schedule, is effective for treatment, prevention or reduction of pain. This dosage varies depending upon the health and physical condition of the individual to be treated, age, degree of analgesia desired, and other relevant factors. It is expected that the amount will fall in a relatively broad range that can be determined through routine trials. "Preventing" or "prevention" herein does not require absolute success in the sense of an absolute prevention of pain but indicates a reduced risk of developing a painful condition or developing pain with reduced severity. Likewise, "treatment" shall not be construed as an absolute cure, but may also relate to amelioration or suppression of pain or pain associated conditions.

Embodiment 1. Compounds that are antagonists of the slow delayed rectifier Kv1.3 channel, pharmaceutical salts or prodrug thereof for use as analgesic in the treatment, prevention or reduction of chronic pain and acute pain.

Embodiment 2. Compounds that are antagonists of the slow delayed rectifier Kv1.3 channel, pharmaceutical salts or prodrug thereof for use as analgesics in the treatment, prevention or reduction of chronic pain and acute pain, wherein said compounds have an affinity 2.5 times greater for Kv1.3 channel than for any other Kv1.x channel, specifically Kv1.1, Kv1.2, Kv1.4, Kv.1.5, Kv1.6 and Kv1.7.

Embodiment 3. Compounds that are antagonists of the slow delayed rectifier Kv1.3 channel, pharmaceutical salts or prodrug thereof for use in the treatment, prevention or reduction of pain, wherein the compounds are at least one of nitenin, PSORA-4, PAP-1, AM92016 hydrochloride, their analogues, salts, or combinations thereof.

Embodiment 4. Compounds that are antagonists of the slow delayed rectifier Kv1.3 channel, pharmaceutical salts or prodrug thereof are used in warm-blooded vertebrates, preferably mammals, more preferably humans.

Embodiment 5. Compounds that are antagonists of the slow delayed rectifier Kv1.3 channel, pharmaceutical salts or prodrug thereof for use in the treatment, prevention or reduction of pain in an individual in need thereof, more specifically with acute or chronic pain. Acute and chronic pain is intended to include, but is not limited to, at least one of the following: neuropathic pain, nociceptive pain, psychogenic or somatogenic pain, diabetic neuropathic pain, post-herpetic pain, low-back pain, radiculopathy pain, musculoskeletal pain, post-operative and post-traumatic pain, phantom pain, surgical pain, wound associated pain, chemotherapy-induced peripheral neuropathic pain, short-term/acute or long-term/chronic inflammatory pain, rheumatic pain, arthritic pain, pain associated with osteoarthritis, myofascial pain, migraine, orofacial chronic pain, trigeminal neuralgia, pain associated with cancer, pain associated with fibromyalgia, hyperalgesia syndromes, pain associated with infections, HIV related pain, sprains and strains, hyperalgesia, somatogenic pain, psychogenic pain, heat induced pain, physical pain, nociceptive pain, rheumatic pain, headache, pelvic pain, myofascial, vascular pain, migraine wound, wound associated pain, arthritic pain, somatic visceral pain, phantom pain, radiculopathy, lumbar pain, visceral pain, bowel pain, bladder pain and pain associated with osteoarthritis.

Embodiment 6. A pharmaceutical composition comprising a pharmacologically acceptable diluent or carrier and a combination of active ingredients (e.g, excipients), wherein said active ingredients comprise a therapeutically effective dosage of at least one of nitenin, PSORA-4, PAP-1, AM92016 hydrochloride or a pharmacologically acceptable salt or prodrug thereof.

Embodiment 7. A method of treating chronic pain or acute pain in a subject in need thereof, comprising administering to the subject a therapeutically effective amount of a compound that is an antagonist of the slow delayed rectifier Kv1.3 channel.

Embodiment 8. The method of embodiment 7, wherein said compound has an affinity 2.5 times greater for a Kv1.3 channel than for any other Kv1.x channel, by at least one affinity-measuring method.

Embodiment 9. The method of any one of embodiments 7 and 8, wherein the compound is chosen from nitenin, PSORA-4, PAP-1, AM92016 hydrochloride, their analogues, salts, or combinations thereof.

Embodiment 10. The method of any one of embodiments 7 through 9, wherein the subject is a warm-blooded vertebrate, preferably a mammal, more preferably a human.

Embodiment 11. The method of any one of embodiment 7 through 10, wherein the acute and chronic pain are chosen from neuropathic pain, nociceptive pain, psychogenic or somatogenic pain, diabetic neuropathic pain, post-herpetic pain, low-back pain, radiculopathy pain, musculoskeletal pain, post-operative and post-traumatic pain, phantom pain, surgical pain, wound associated pain, chemotherapy-induced peripheral neuropathic pain, short-term/acute or long-term/chronic inflammatory pain, rheumatic pain, arthritic pain, pain associated with osteoarthritis, myofascial pain, migraine, orofacial chronic pain, trigeminal neuralgia, pain associated with cancer, pain associated with fibromyalgia, hyperalgesia syndromes, pain associated with infections, HIV related pain, sprains and strains, hyperalgesia, somatogenic pain, psychogenic pain, heat induced pain, physical pain, nociceptive pain, rheumatic pain, headache, pelvic pain, myofascial, vascular pain, migraine wound, wound associated pain, arthritic pain, somatic visceral pain, phantom pain, radiculopathy, lumbar pain, visceral pain, bowel pain, bladder pain and pain associated with osteoarthritis.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

Abbreviations $Ca^{2+}$: Calcium
$Ca_V$: Voltage-gated calcium channel
CCI: Chronic Constriction Injury
CFA: Complete Freund's Adjuvant
CHO: Chinese hamster ovary
CIPN: Chemotherapy-induced Peripheral Neuropathy
CNS: Central nervous system
COP: Chronic orofacial pain
DRG: Dorsal root ganglion
ECG: Electrocardiogram
HEK: Human embryonic kidney
hERG: Human Ether-à-go-go-Related Gene—Kv11.1
HFF2: Human foreskin fibroblasts 2
I: current
$I_{fast}$: Fast current component
$I_{slow}$: Slow current component
IV: Intravenous
$K^+$: Potassium
$K_V$: voltage-dependent potassium channel
$K_v1.x$: voltage-dependent potassium channel subunits, given by x
L: Lumbar
$Na^+$: Sodium
$Na_V$: Voltage-gated sodium channel
$Na_v1.x$: voltage-dependent sodium channel subunits, given by x
NSAID(s): non-steroidal anti-inflammatory drug(s)
MTS: (3-(4,5-dimethylthiazol-2-yl)-5-(3-carboxymethoxyphenyl)-2-(4-sulfophenyl)-2H-tetrazolium)
PAP1: 5-(4-Phenoxybutoxy)psoralen
PSORA 4: 4-(4-Phenylbutoxy)-7H-furo[3,2-g][1]benzopyran-7-one
sdDRGN: small diameter dorsal root neurons
sdTGN: small diameter trigeminal ganglion neurons
STZ: Streptozotocin
TG: Trigeminal Ganglion
TRP: Transient Receptor Potential Cation channel
TRPV1: Transient Receptor Potential Cation channel subfamily
USA: United States of America
V member 1
V: Voltage
Vh: Voltage of half maximum current Compounds of the disclosure, pharmaceutically acceptable salts of said compounds, and/or pharmaceutical compositions comprising said compounds and/or pharmaceutically acceptable salts thereof can be administered as therapeutic treatments. Said compounds, pharmaceutically acceptable salts, and/or pharmaceutical compositions can be administered in unit forms of administration to mammalian subjects, including human beings. Suitable unit forms of administration include, as non-limiting examples, forms administered orally and forms administered via a parenteral route, non-limiting examples of which including inhalation, subcutaneous administration, intramuscular administration, intravenous administration, intradermal administration, and intravitreal administration.

In some embodiments, pharmaceutical compositions for oral administration can be in the form of tablets, pills, powders, hard gelatine capsules, soft gelatine capsules, and/or granules. In some embodiments of such pharmaceutical compositions, a compound of the disclosure and/or a pharmaceutically acceptable salt of a compound of the disclosure is (or are) mixed with one or more inert diluents, non-limiting examples of which including starch, cellulose, sucrose, lactose, and silica. In some embodiments, such pharmaceutical compositions may further comprise one or more substances other than diluents, such as (as non-limiting examples), lubricants, coloring agents, coatings, or varnishes.

The pharmaceutical compositions of the disclosure may comprise pharmaceutically acceptable carriers, excipients, vehicles, and diluents. Many of these are well-known to persons having ordinary skill in the art and are described in, as a non-limiting example, *Remington: The Science and Practice of Pharmacy,* 22nd Edition, Lippincott Williams & Wilkins, Philadelphia, Pa. (2013) and any other editions, which are hereby incorporated by reference.

In one aspect, this disclosure relates to the use of Kv1.3 antagonists as analgesics for the treatment, prevention or reduction of chronic and acute pain. Through an approach using physiology and pharmacology of ionic currents/channels, a novel pharmaceutical application regarding an analgesic effect for several types of pain is disclosed herein.

In sharp contrast to the existing therapeutic drugs, the analgesic compounds disclosed herein will be positioned as a breakthrough in pain management due to its novel mode of action, and predicted effectiveness in humans, target specificity, and reduced side-effects. The nitenin, PSORA-4, PAP-1 and AM92016 hydrochloride (four examples of Kv1.3 antagonists) act specifically on slow delayed rectifier Kv channels, expressed in the pain-sensing c-fibers of the dorsal root ganglia and of the trigeminal ganglia. Without being bound by theory, it is proposed that the mode of action of these drugs involves a channel blockage (rather than opener like Retigabine) and has advantageous particularities, such as: (a) involves a change of the inactivation state of the channel, and, (b) acts particularly on a set of $K_V$ channels, mainly Kv1.3. This novel mode of action explains why and how Kv1.3 antagonists are solely effective in body limbs/body parts with injured/affected nerves. Additionally, such drugs do not alter nociceptive and sensorial scores, in unaffected body limbs/body parts.

The present disclosure discloses robust evidence that compounds that act as antagonists of the delayed rectifier Kv1.3 channel may be used as analgesics for the treatment, prevention or reduction of chronic and acute pain. This evidence was obtained from several technical approaches, including an ex vivo neuronal preparation, animal model of pain, behavioural readouts of pain, and, whole-cell voltage-clamp recordings. These experimental results disclosed herein concern four different exemplary Kv1.3 blockers; nitenin, PSORA-4, PAP-1 and AM92016 hydrochloride.

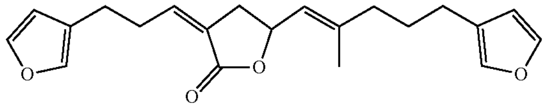

Nitenin

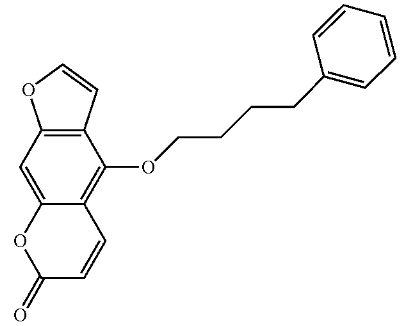

Psora-4

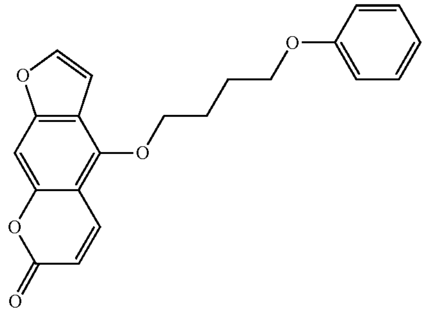

PAP-1

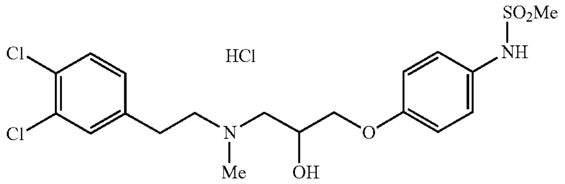

AM92016 hydrochloride

The nitenin compound used as an example of the present disclosure was isolated/purified from the marine sponge *Spongia agaracina* captured in Sagres, Portugal, whereas PSORA-4, PAP-1 and AM92016 hydrochloride were acquired commercially, and are described as antagonists of slow delayed rectifier $K^+$ channels, being PSORA-4 and PAP-1 mentioned as specific blockers for Kv1.3. As shown in the EXAMPLES, Nitenin, PSORA-4, PAP-1 and AM92016 showed the capacity of modulating the $K^+$ currents recorded from sdDRGNs (pain sensing neurons). Results were also confirmed in small diameter trigeminal ganglion neurons (sdTGNs) that showed identical pharmacological effects in very similar $K^+$ current profiles.

The $K^+$ currents affected by the identified compounds, recorded from sdDRGNs (and sdTGNs) by whole-cell voltage-clamp techniques, were object of intensive research by the applicant in the area of pain neurophysiology. The use of rat pain models was fundamental to perform previous target validation, i.e., to determine the $K^+$ current component differentially expressed in pain conditions. In one aspect of the disclosure, it is suggested that the $K^+$ current component affected with pain condition is the one principally modulated (diminished) by the compound(s) of interest. The nature of the recorded modulatory effect on the currents was studied by monitoring several biophysical parameters, such as voltage dependencies of activation and inactivation and kinetics. The specificity of the bioactivity was carried out by comparing the pharmacological effect on currents recorded from the sdDRGNs with those in other types of dorsal root ganglia (medium and large diameter DGRs).

Additionally, nitenin is mostly active on hKv1.3 ($IC_{50}$~190 nM), which is 6 to 30 times more sensitive than the other Kv1.xs tested (Kv1.1, Kv1.2, Kv1.3, Kv1.4 and Kv1.6). For PSORA-4 and PAP-1, both are mostly active for Kv1.3 ($IC_{50}$~2-3 nM), which is ~2.5 times (for the case of PSORA-4) to ~20 times (for the case of PAP-1) more sensitive than the other Kv tested. (Vennekamp et al., 2004; Schmitz et al. 2005)

One of the competitive advantages of nitenin, PSORA-4, PAP-1, AM92016 hydrochloride and other Kv1.3 blocking compounds over other compounds used in pain therapy, including those acting on ion channels, lies, in part, in at least 6 principal particularities that, although inter-related can be described as follows:

1—The novel mode of action attributed to the Kv1.3 antagonists disclosed herein, as well as the location and nature of their cellular target: Kv1.3 blockers reduce the activity of $K_V$ channels expressed in snDRGs (and snTGs), responsible for part of the slow delayed rectifying current, which modulate pain signalling and propagation towards the brain. The fact that there is currently a huge need for specific blockers of such Kv1.3 channels for clinical potential, particularly in what concerns in their potential for auto-imine diseases, will potentiate the development of future related products.

2—Administering specific Kv1.3 blockers compounds does not result in any loss of sensorial and nociceptive capacities and nociception of the uninjured limbs/body parts, a feature that relates to the mode of action, for example, to the fact that it an activity-dependent effect.

3—The Kv1.3 blockers of the present disclosure are easily administrated. In the animal models used to test Kv1.3 blocking compounds, peripheral intravenous (IV) and intraperitoneal injections were used with success regarding the analgesic effect of these compounds.

4—Kv1.3 antagonists are effective on mitigating pain in acute and chronic neuropathic chronic pain. Such results anticipate a wide range of possible clinical applications.

5—Although also effective in acute/short-term pain, Kv1.3 antagonists are particularly effective on long-term/chronic forms of pain.

6—By acting specifically in a subset of potassium channels (Kv1.x), and having little or no effect on sodium currents/channels ($Na_v$s), the specific Kv1.3 blocking compounds will not compete with Nav modulatory agents but rather, they may eventually be applied in combination with those, maximising the envisaged analgesic effect or acting in a synergistically manner.

In one embodiment, the compounds of the disclosure, or pharmaceutically acceptable salts and prodrugs thereof may be used to treat acute pain. Examples of situations of acute pain include those derived from surgery, broken bones, dental work, burns and cuts, labor and childbirth.

In one embodiment, the compounds of the disclosure, or pharmaceutically acceptable salts and prodrugs thereof may be used to treat chronic pain. Examples of diseases or disorders associated with chronic pain include peripheral neuropathy chronic, diabetes, arthritis, fibromyalgia, cancer, back pain, shingles, trigeminal neuralgia and previous trauma or injury.

In some embodiments, the compounds of the disclosure, or pharmaceutically acceptable salts and prodrugs thereof, can be used to treat hyperalgesia, somatogenic pain, psychogenic pain, heat induced pain, physical pain, nociceptive pain, rheumatic, headache, pelvic pain, myofascial, vascular pain, migraine wound, wound associated, arthritic, somatic visceral, phantom pain, radiculopathy, lumbar pain, or pain associated with osteoarthritis.

Both acute and chronic pain involve the complex alteration of the processing and conduction of electrical signals from peripheral nerves to the central nervous system (CNS). The electrical excitability and activity levels of a normal condition, or those related to chronic pain, are result of the inflow or outflow of charged metal ions such as sodium ($Na^+$), potassium ($K^+$) or calcium ($Ca^{2+}$) through membrane ion channels (Nav, Kv or Cav, respectively), causing the generation, propagation and transmission of electric signals throughout the cell and from cell to cell. In chronic pain, the neuronal network underlying pain signalling is altered, with abnormal ionic currents brought by altered expression and biophysics of the underlying channels, resulting in excessive and sustained neuronal excitability and activity. Therefore, an effective analgesic would need to be able to suppress the hyperexcitability of the pain signalling network, restoring the physiologic expression and/or biophysical profiles of the functioning channels, and, in turn, restoring the network activity to resting levels.

Small-diameter DRG neurons (c-fibers), also called pain-sensing neurons, are located outside of the spinal cord that carry the nociceptive input to the CNS (i.e, leading to ‘pain’). Usually, in normal conditions, these neurons do not have spontaneous firing activity—they are silent (e.g Ly et al., 2018)—, a situation that changes during pain episodes and, indeed with chronic pain. The present underlying therapeutic strategy is to target key ion channels localized in such neurons in the DRG neurons and those in trigeminal ganglia (TG), to “switch-off” such ‘pain-induced’ hyperexcitability. Consequently, the transmission of the “pain signal” to the CNS is interrupted or diminished, preventing, this way, brain perception of pain.

In some embodiments, the compounds of the disclosure, or pharmaceutically acceptable salts and prodrugs thereof may be used to halt pain-induced hyperexcitability. In some embodiments, they can be used to modulate the brain's perception of pain.

Several ion channels have been identified as key effectors in pain propagation. Some are particularly present in these pain-sensing neurons. Therefore, specifically modulating their activity would block pain without affecting other body functions. It is disclosed herein that Kv1.3 antagonists are specific modulators of slow delayed rectifier voltage-activated $K^+$ currents recorded from sdDRGNs and sdTGNs, (thought to correspond with c-fibers). This effect is lower in large diameter neurons at a sub micromolar concentration range, i.e. at concentrations below 1 micromolar, the modulatory effect of Kv1.3 blockers is more obvious for sdDRGNs and sdTGNs.

In some embodiments, the compounds of the disclosure, or pharmaceutically acceptable salts and prodrugs thereof may be used to modulate slow-voltage activated $K^+$ currents. In some embodiments, the currents are from the small diameter (sdDRGNs also sdTGNs) neurons.

Kv1.x, including those mediating slow voltage-activated currents, and the Kv1.3 type, are ion channels involved in pain signal propagation as principally present in pain-sensing neurons. The nitenin, PSORA-4 and AM92016 hydrochloride compounds tested herein are particularly effective on the slow $K^+$ current-component which, consequently must underlie the activity of Kv1.3 channels.

In some embodiments, the compounds of the disclosure, or pharmaceutically acceptable salts and prodrugs thereof may be used as blockers of Kv1.3. Kv1.3 has been described as a target for treatment of immunological related pathologies as well as a target for treatment of diabetes and other metabolic disorders. The compounds of the disclosure may be used in the treatment of diabetes and other metabolic disorders.

In some embodiments, the compounds of the disclosure, or pharmaceutically acceptable salts and prodrugs thereof may be used as anti-inflammatory agents and to treat auto-immune diseases. In other embodiments, they may be used to increase insulin sensitivity.

With regard to these therapeutic treatments, the mode (or modes) of administration, dosage (or dosages), and optimized pharmaceutical form (or forms) can be determined according to criteria generally considered during the establishment of a treatment of a patient, such as, by way of non-limiting examples, the potency of the compound(s) and/or pharmaceutically acceptable salts of the compound (s), the age of the patient, the body weight of the patient, the severity of the patient's condition (or conditions), the patient's tolerance to the treatment, and secondary effects observed in treatment. Determination of dosages effective to provide therapeutic benefit for specific modes and frequency of administration is within the capabilities of those skilled in the art.

Examples

In Vivo and Ex Vivo Pain Models

The rat pain models used for both in vivo behaviour work and for the electrophysiological ex vivo studies were:

- Naïve Wistar: control rats; neurons from the dorsal root ganglia (DRG), lumbar 4, 5 and 6 (L4, L5 and L6).
- Acute and chronic neuropathic pain rat model: CCI rats (chronic constriction of the sciatic nerve of Wistar rats) 3 days (for acute) and 23 to 29 days (for chronic) after surgery; neurons from DRGs (L4, L5 and L6).

For the electrophysiological recordings of the ex vivo material, voltage-clamp recordings were performed on neurons isolated from rat DRGs (and TGs). Recordings were performed from the soma that often contained the proximal fraction of axon, 1 hour after the end of the cell isolation process (includes enzymatic and mechanical treatment).

Mode of Action

The mode of action of Kv1.3 antagonists as analgesics is disclosed herein for the first time. It involves reduction of $K^+$ currents rather than their potentiation. For such reason, it is important to characterise first the potassium currents present in the sdDRGNs and in sdTGNs.

The voltage activated whole-cell $K^+$ currents recorded from sdDRGNs upon a depolarizing step (say, to +40 mV lasting a second, as in FIG. 1-4) showed a fast activation followed by two phases of inactivation. The current decay at depolarised potentials are thus better fit by a sum of two exponential functions: a relatively fast component (here termed $I_{fast}$—associated to what is known as A-current), showing a time course ($\tau_{fast}$) of tens of milliseconds, followed by a much slower inactivating current (here termed $I_{slow}$), showing a time course ($\tau_{slow}$) of hundreds of milliseconds. Different proportion for $I_{fast}$ and $I_{slow}$ are found from cell to cell and even some cells show only one component, $I_{slow}$ The currents found in sdDRGns are very similar to those described for sdTGns.

Experiments using nitenin, PSORA-4, PAP-1 and AM92016 hydrochloride showed that all inhibit the $K^+$ currents from sdDRGNs (and from sdTGNs) in a dose dependent manner. Under moderate concentrations, the effects are specific on $I_{slow}$ In the case of nitenin, concentrations up to 1 μM (~0.3 μg/ml), it specifically reduces $I_{slow}$ (see FIG. 1); in the case of PSORA, at concentrations of up to 3 nM (1 ng/ml), it specifically reduces $I_{slow}$ (see FIG. 2); in the case of PAP-1, at concentrations up to 2 nM (~0.7 ng/ml), it specifically reduces $I_{slow}$ (see FIG. 3; and in the in the case of AM92016 hydrochloride, concentrations of 40 nM (~19.4 ng/ml), it specifically reduces $I_{slow}$ (see FIG. 4. Hence, all act preferentially on $I_{slow}$, current component of which becomes over expressed (in relation to $I_{slow}$), in sdDRGn neurons (and in sdTGns) obtained from 'injured nerves' from chronic pain rat models (CCI, CFA and Orofacial). In the typical example presented in FIG. 1-4, one can note that the peak current is mostly unaltered by the treatment nitenin, PSORA-4, PAP-1 or by AM92016 hydrochloride, whereas the slower component is indeed reduced. The nitenin, PSORA-4, PAP-1 and AM92016 hydrochlorid sensitive current-components (trace subtraction at the bottom of FIG. 1-4) shows current decays that is better fit by a single exponential of few hundred of milliseconds, further suggesting that, at moderate concentrations, the effects are specific on $I_{slow}$. In contrast, $I_{fast}$, was unaffected by any of the Kv1.3 antagonists at concentrations up to those referred above. Importantly, reductions of $I_{slow}$ evoked by any of the Kv1.3 antagonists used, were larger in neurons obtained from chronic pain animals when compared from the reductions evoked by same concentrations in neurons obtained from 'control' animals.

The higher sensitivity of Kv1.3 antagonists to $I_{slow}$ (rather than $I_{fast}$) and the nature of the Kv1.3 antagonists sensitive currents (see current subtractions in FIG. 1-4) reinforces that in the concentrations used, each antagonist is affecting a single current component and, consequently, one channel population (allegedly Kv1.3).

The inhibition of slow $K^+$ currents by the Kv1.3 antagonists involves a change in the voltage dependence of steady state of inactivation (In fact, all the Kv1.3 antagonists evoked shifts to more hyperpolarised potentials the I-V curves related to the voltage dependence of inactivation (see FIG. 5-8).

Thus, the compounds inhibit slow voltage-activated currents recorded from sdDRGNs by promoting $K^+$ channel inactivation, which is impaired in chronic pain conditions. More precisely, the compounds shift the voltage sensitivity of the steady-state inactivation to less depolarised values (or more hyperpolarised), facilitating inactivation. Such compound-evoked shift is as higher as more depolarised the voltage curve profile is in the first place (voltage dependence of inactivation). Depolarised Inactivation curves are typical from sdDRGNs obtained from chronic pain conditions. In other words, in neurons obtained from injured nerves (chronic), Kv1.3 antagonists revert the voltage dependence profile of inactivation to 'control' patterns. Consequently, the compound-evoked shifts in the voltage sensitivity of inactivation is higher in neurons from injured nerves (that exhibit an abnormally depolarized profile) and lower/inexistent in unaffected neurons that show hyperpolarised voltage profiles. This interesting effect on channel gating explains in part the compound-evoked decrease of neuronal excitability that is specific/more pronounced in affected neurons, i.e. during pain.

C fibers are usually silent, with little or no spontaneous firing activity, i.e., there is no basal activity in control conditions. We start by analysing the effect of Kv1.3 antagonists on the un-injured silent neurons. Given the nature of the mode of action of Kv1.3 antagonists, one would expect little or no effect on $K^+$ currents in such 'silent neurons', because, the compounds evoked shift in inactivation curves are minimal in the un-injured neurons. Nevertheless, in this case of unaffected neurons, there is moderate decrease of $K^+$ currents, but such effect would not reach a threshold potential for inducing repetitive firing (due to insufficient evoked depolarization). This explains in part why Kv1.3 antagonists do not change the "pain perception" in non-affected body regions. On the other hand, in the occurrence of chronic pain, there is an hyperexcitable state in the injured neurons, with repetitive and sustained firing. In this hyperexcitable neurons, in which there is 'potentiation of channel inactivation' (brought by depolarised curves of the voltage dependence of steady-state of inactivation), the effects of Kv1.3 antagonists are maximal. A further increase of the resting potential (induced by the Kv1.3 antagonist-induced reduction of $K^+$ currents) will dictate a firing failure brought by indirect promotion of inactivation of sodium channels. The signal is therefore interrupted but only on the 'injured' fibers.

How the effects of Kv1.3 antagonists on Kv currents results in the analgesic effect consists in a new mode of action because, in a conventional way to address this matter, one would expect that an increase of $K_V$ currents, rather than an inhibition, would calm down neuroexcitability of the hyperexcitable C fibers. In the present case, one must stress that slowly inactivating-potassium currents ($I_{slow}$) are somehow exacerbated in chronic pain conditions (in comparation with a diminished $I_{fast}$) (sdDRGns obtained from CCI, CFA and STZ, and, sdTGns from COP rat model); also, in such conditions, $I_{slow}$ shows abnormal depolarised inactivation profiles, i.e. channels inactivating less. In order to sustain repetitive firing for long periods, the typical situation under chronic pain, the increase of the "excitatory force" brought by the consensual increase in $Na^+$ currents, has to be sustained by a counter-balancing increase in $K^+$ currents that would accommodate repetitive—long-term firing patterns. The effect of the compounds disclosed herein is such that it reverts such patterns to control profiles, decreasing the slowly-inactivating Kv-mediated current. This Kv1.3 antagonist-evoked effect of the slow $K^+$ currents would not allow the required accommodation of the increase of sodium conductance (Nav), typical in pain situations. As a result, the exacerbated sodium currents would inactivate in the presence of a Kv1.3 antagonist (also due to a depolarization evoked by the decrease of Kv currents), switching off spike firing in the affected nerves but not in normal, uninjured neurons.

This means that, during pain, namely, in chronic pain, Kv blockers, and not only the Kv potentiators or openers, should be considered as potential analgesics.

How a reduction of $K^+$ currents result in a marked decrease of neuronal excitability can be explained in different ways or, most likely, by a combination of phenomena. Firstly, as mentioned above, the Kv1.3 antagonist-induced decrease of $K^+$ currents may result in a slow depolarization of the affected neurons in a way that membrane potential is kept at a depolarized level, so the usual threshold potential may pass without an action potential having been fired. It would thus result in an accommodation-like process as depolarization would close inactivation gates of the $Na^+$ channels, remaining closed, preventing the upstroke of action potential to occur (not enough $Na^+$ channels 'activatable').

Secondly, one may consider a more direct role of the specific blockage on Kv1.3, as (1) the Kv1.3 antagonists are particularly effective on Kv1.3 channels and (2) Kv1.3 expressed in DRG (Yang et al., 2004) and increases it expression levels in DRG neurons with chronic pain (unpublished data). The biophysical nature and the kinetics of Kv1.3 mediated currents are thought to sustain stabilised tonic firing (Kupper et al., 2002), a state that correspond to neurons in a 'chronic pain situation'. Reducing such Kv1.3 mediated currents would lead to a decrease in action potential amplitudes and into a stationary depolarised state with no firing, as found in rat hippocampal neurons (Kupper et al., 2002).

Efficacy Results

For efficacy studies, nociception was assessed in animals by regular behavioural monitoring, by quantifying the sensitivity to mechanical stimuli with Von Frey filaments, and consequently reflecting hyperalgesia when hypersensitive. For the Neuropathic pain model CCI, the cold allodynia with acetone test was also used and showed very similar responses as those with Von Frey Filaments.

Efficacy after intravenous administration of Kv1.3 antagonists. The following results concern intravenous (IV) injections of purified nitenin (>98%) (1 μg/mL of blood ~0.06 mg/Kg) PSORA-4 (30 μg/mL of blood ~1.8 mg/Kg), PAP-1 (30 μg/mL of blood ~1.8 mg/Kg) and AM92016 hydrochloride (2.9 μg/mL of blood ~0.17 mg/Kg).

Naïve Wistar controls: There was never any change in sensitivity scores following IV injections of nitenin, PSORA-4, PAP-1 and AM92016 hydrochloride for both paws.

With CCI rats, following IV administrations, there was a noticeable decrease of sensitivity to mechanical stimuli for both acute (3 days after induction of the model) and chronic (22 to 31 days) situations. Typical experiments for chronic conditions are presented in FIGS. 5 to 8. The Kv1.3 antagonists-induced decreases of hypersensitivity was noticeable in both cases (acute and chronic) but clearly higher in the case of chronic pain; in some individuals the scores were reverted to control values. The duration of the pain mitigation lasted for 2 to 4 hours. Importantly, there were no changes in the behavioural scores of the contralateral (uninjured) paw for all the animals tested.

In summary, nitenin, PSORA-4, PAP-1 and AM92016 hydrochloride (Kv1.3 blockers) have shown to be effective for short-term/acute and long-term/chronic neuropathic pain. Efficacy has been demonstrated for with intravenous administration, but for some antagonists such as nitenin, intraperitoneally and, importantly, via oral administration was also successful.

Based in dose dependent curves, where several concentrations were applied IV and efficacy levels were consequently quantified, nitenin and analogues should be used for pharmacological use in warm-blooded vertebrates, particularly humans, in doses ranging from 0.1 μg/ml blood (6 μg/Kg body weight) to 30 μg/ml blood (1.8 mg/Kg body weight); PSORA-4 should be used for pharmacological use in warm-blooded vertebrates, particularly humans, in doses ranging from 1 μg/ml blood (60 μg/Kg body weight) to 300 μg/ml blood (18 mg/Kg body weight); PAP-1 should be used for pharmacological use in warm-blooded vertebrates, particularly humans, in doses ranging from 1 μg/ml blood (60 μg/Kg body weight) to 300 μg/ml blood (18 mg/Kg body weight); AM92016 hydrochloride should be used for pharmacological use in warm-blooded vertebrates, particularly humans, in doses ranging from 0.1 μg/ml blood (6 μg/Kg body weight) to 300 μg/ml blood (18 mg/Kg body weight).

Several features are described hereafter that can each be used independently of one another or with any combination of the other features. However, any individual feature might not address any of the problems discussed above or might only address one of the problems discussed above. Some of the problems discussed above might not be fully addressed by any of the features described herein. Although headings are provided, information related to a particular heading, but not found in the section having that heading, may also be found elsewhere in the specification.

BIBLIOGRAPHIC REFERENCES

Altun A, Ozdemir E, Yildirim K, Gursoy S, Durmus N and Bagcivan I (1015) The effects of endocannabinoid receptor agonist anandamide and antagonist rimonabant on opioid analgesia and tolerance in rats. Gen. Physiol. Biophys. (2015), 34, 433-440 433

Li Y, North R Y, Rhines L D, Tatsui C E, Rao G, Edwards D D, Cassidy R M, Harrison D S, Johansson C A, Zhang H, Dougherty P M. (2018). DRG Voltage-Gated Sodium Channel 1.7 Is Upregulated in Paclitaxel-Induced Neuropathy in Rats and in Humans with Neuropathic Pain. J Neurosci. 2018 Jan. 31; 38(5): 1124-1136.

Kupper J, Prinz A A, Fromherz P (2002). Recombinant Kv1.3 potassium channels stabilize tonic firing of cultured rat hippocampal neurons. Pflugers Arch. February; 443(4):541-7.

Remington: The Science and Practice of Pharmacy, 22nd Edition, Lippincott Williams & Wilkins, Philadelphia, Pa. (2013) and any other editions Schmitz A, Sankaranarayanan A, Azam P, Schmidt-Lassen K, Homerick D, Hänsel W and Wulff H (2005). Design of PAP-1, a Selective Small Molecule Kv1.3 Blocker, for the Suppression of Effector Memory T Cells in Autoimmune Diseases. Molecular Pharmacology November, 68 (5) 1254-1270.

Vennekamp J, Wulff H, Beeton C, Calabresi P A, Grissmer S, Hänsel W, Chandy K G (2004). Kv1.3-blocking 5-phenylalkoxypsoralens: a new class of immunomodulators. Mol Pharmacol. 65(6):1364-74.

Yang E K, Takimoto K, Hayashi Y, de Groat W C, Yoshimura N. (2004). Altered expression of potassium channel subunit mRNA and alpha-dendrotoxin sensitivity of potassium currents in rat dorsal root ganglion neurons after axotomy. Neuroscience; 123(4):867-74.

What is claimed is:

1. An analgesic composition comprising a pharmacologically acceptable diluent or carrier and a therapeutically effective amount of one or more compounds that are antagonists of the slow delayed rectifier Kv1.3 channel, or pharmaceutical salts thereof, wherein the compound is an antagonist of the slow delayed rectifier Kv1.3 channel when the compound inhibits one or more slow delayed rectifier Kv1.3 channels, as evaluated by measuring the effect of the compound on slow delayed rectifier voltage-activated K+ currents recorded from small-diameter dorsal root neurons (DRG) neurons and/or small diameter trigeminal ganglia (TG) neurons; wherein one or more of the compounds have an affinity at least 2.5 times greater for the human Kvl1.3 channel than for any other human Kv1.1 channel, human Kv1.2 channel, human Kv1.4 channel, human Kv1.5 channel, human Kv1.6 channel, and human Kv1.7 channel, as measured by voltage clamp recordings of currents evoked by cells that express solely said channel; and wherein the compound is not AM92016 hydrochloride.

2. The analgesic composition according to claim 1, wherein one or more of the compounds is selected from nitenin, PSORA-4, PAP-1, their salts, and combinations thereof.

3. A method of treating chronic pain or acute pain in a subject in need thereof, comprising administering to the subject a therapeutically effective amount of a compound that is an antagonist of the slow delayed rectifier Kv1.3 channel, or a pharmacologically acceptable salt thereof, wherein the compound is an antagonist of the slow delayed rectifier Kv1.3 channel when the compound inhibits one or more slow delayed rectifier Kv1.3 channels, as evaluated by measuring the effect of the compound on slow delayed rectifier voltage-activated K+ currents recorded from small-diameter dorsal root neurons (DRG) neurons and/or small diameter trigeminal ganglia (TG) neurons, wherein the compound is not AM92016 hydrochloride.

4. The method of claim 3, wherein said compound has an affinity at least 2.5 times greater for the human Kv1.3 channel than for any other human Kv1.1 channel, human Kv1.2 channel, human Kv1.4 channel, human Kv1.5 channel, human Kv1.6 channel, and human Kv1.7 channel, as measured by voltage clamp recordings of currents evoked by cells that express solely said channel.

5. The method of claim 3, wherein the compound is chosen from nitenin, PSORA-4, and PAP-1, their salts, and combinations thereof.

6. The method of claim 5, wherein the subject is a mammal.

7. The method of any one of claims 3 to 6, wherein the acute and chronic pain are chosen from neuropathic pain, nociceptive pain, psychogenic or somatogenic pain, diabetic neuropathic pain, post-herpetic pain, low-back pain, radiculopathy pain, musculoskeletal pain, post-operative and post-traumatic pain, phantom pain, surgical pain, wound associated pain, chemotherapy-induced peripheral neuropathic pain, short-term/acute or long-term/chronic inflammatory pain, rheumatic pain, arthritic pain, pain associated with osteoarthritis, myofascial pain, migraine, orofacial chronic pain, trigeminal neuralgia, pain associated with cancer, pain associated with fibromyalgia, hyperalgesia syndromes, pain associated with infections, HIV related pain, sprains and strains, hyperalgesia, somatogenic pain, psychogenic pain, heat induced pain, physical pain, nociceptive pain, rheumatic pain, headache, pelvic pain, myofascial, vascular pain, migraine wound, wound associated pain, arthritic pain, somatic visceral pain, phantom pain, radiculopathy, lumbar pain, visceral pain, bowel pain, bladder pain, and pain associated with osteoarthritis.

8. The method of claim 6, wherein the mammal is a human.

* * * * *